United States Patent [19]

Risteli et al.

[11] Patent Number: 5,538,853
[45] Date of Patent: Jul. 23, 1996

[54] BONE RESORPTION ASSAY BASED ON A PEPTIDE LIBERATED DURING COLLAGEN DEGRADATION

[75] Inventors: Juha P. Risteli; Leila T. Risteli, both of Oulu, Finland

[73] Assignee: Orion Corporation, Orion Diagnostica, Koivumankkaankuja, Finland

[21] Appl. No.: 274,105

[22] Filed: Jul. 12, 1994

Related U.S. Application Data

[63] Continuation of Ser. No. 855,195, Mar. 20, 1992, abandoned.

[30] Foreign Application Priority Data

Mar. 20, 1991 [GB] United Kingdom ............... 9105893

[51] Int. Cl.$^6$ .................... G01N 33/53; G01N 33/535
[52] U.S. Cl. .................... 435/7.9; 435/7.92; 435/7.93; 435/7.94; 435/971; 435/975; 436/536; 436/538; 436/540; 436/808; 530/323; 530/388.1; 530/389.1; 530/391.1; 530/391.3
[58] Field of Search ............................. 435/7.9, 7.92, 435/7.93, 7.94, 971, 975, 70.21, 240.27; 436/518, 536, 538, 540, 542, 804, 805, 808; 530/388.1, 389.1, 391.1, 391.3, 323

[56] References Cited

U.S. PATENT DOCUMENTS 4,973,666  11/1990  Eyre .................... 530/323

FOREIGN PATENT DOCUMENTS 2205643  12/1988  United Kingdom .

OTHER PUBLICATIONS

Kuhn, "Chemical Properties of Collagen", in *Immunochemistry of the Extracellular Matrix*, H. Furthmayr, Ed., CRC Press, Inc., Boca Raton, Fla. (1982), pp. 1–29.

Hartmann et al., "Radioimmunoassay of Type I Collagen that Mainly Detects Degradation Products in Serum: Application to Patients with Liver Disease", *Clin. Chem.* vol. 36, No. 3, pp. 421–426 (1990).

Wu et al., "Fine Powdering Exposes the Mineral–Protected Collagen of Bone to Protease Digestion", *Calcif. Tissue Int.*, vol. 42, pp. 243–247, (1988).

Risteli et al., "Bone Resorption Assay Based on a Peptide Liberated During Type I Collagen Degradation", *J. Bone Min. Res.*, 6 (Supp.1), SZ51(Abstract 670), 1991.

Ericksen et al., "Cross–Linked Carboxyterminal Telopeptide of Type I Collagen in Serum (S–ICTP): A New Bone Resorption Marker", *J. Bone Min Res.*, 6(Suppl), 5243 (Abstract 637), 1991.

*Primary Examiner*—Toni R. Scheiner
*Assistant Examiner*—Susan C. Wolski
*Attorney, Agent, or Firm*—Brumbaugh Graves Donohue & Raymond

[57] ABSTRACT

An antibody raised to type I collagen carboxyterminal cross-linked telopeptide isolated from decalcified human or animal bone, may be used in an assay to determine the concentration of liberated carboxyterminal telopeptide region of the type I collagen molecule in a sample. When the sample is a body fluid such as serum or urine the degradation product measured is resistant to further degradation, since it contains a multivalent intermolecular cross-link, and can thus be found in the body fluid. The assay may be used to assess the degradation of type I collagen, the major organic constituent of bone matrix.

29 Claims, No Drawings

BONE RESORPTION ASSAY BASED ON A PEPTIDE LIBERATED DURING COLLAGEN DEGRADATION

This is a continuation of application Ser. No. 07/855,195, filed on Mar. 20, 1992 now abandoned.

BACKGROUND OF THE INVENTION

This invention relates to an assay for measuring the degradation of type I collagen and thus to assessing the rate of bone resorption, and a kit suitable for carrying out this assay.

Type I collagen is the most abundant collagen type in the human body. It occurs together with other collagen types in soft connective tissues, but it also forms the scaffold of mineralized bone, where it is practically the only collagen type present and where it accounts for about 90% of the total organic material. Type I collagen is also found in the bones of non-human vertebrates.

Throughout life, bone is a metabolically active tissue. The processes of new matrix synthesis and turnover of existing matrix are normally closely coupled to each other with respect to both space and time. In disease states this balance can be disturbed, e.g. in osteoporosis bone resorption in the long run exceeds synthesis, leading to a diminished bone mass. Similarly rheumatoid arthritis and various carcinomas with bone metastases induce local bone destruction.

The amount of type I collagen synthesized can be estimated on the basis of an assay method for the carboxyterminal propeptide of type I procollagen, which is carried out on blood samples. The degradation of collagen has long been assessed by determining urinary hydroxyproline excretion. However, this method is tedious, needs 24 hour urine collection, and is not specific for a particular collagen type. A newer method is the assessment of collagen-derived pyridinoline cross-links in urine. Despite some advantages over the hydroxyproline assay, this method shares its major drawbacks. There is a need for a specific method for determining type I collagen degradation based on serum samples.

SUMMARY OF THE INVENTION

The present invention provides such a method, which is quick and simple to practice.

We have found that during bone collagen degradation, when a number of different fragments are formed, a certain cross-linked fragment is liberated which is resistant to further degradation and retains intact its immunochemical structure. It therefore appears in the circulation in a form which can easily be quantitatively measured using an immunoassay. This carboxyterminal non-helical end of the type I collagen molecule, the so-called telopeptide region, which participates in intermolecular multivalent cross-links in an insoluble collagenous matrix can be assayed by immunological methods, e.g. by a radioimmunoassay, and provides significant information on the degradation of type I collagen.

This discovery can be used in any known method of immunoassay using an antibody specific to the carboxyterminal telopeptide of type I collagen. The invention accordingly provides a method for assaying a type I collagen degradation product, which comprises contacting in any order (i) a sample which is known or suspected to contain such product; (ii) an antibody specific to type I collagen carboxyterminal telopeptide; and (iii) a label; under conditions such that the label becomes bound in an antibody-containing complex an amount which depends on the amount of type I collagen degradation product present in said sample and then assaying the bound and/or unbound label as a measure of the presence or level of type I collagen degradation product in said sample.

Such a method would be of use in assessing collagen degradation in either human or non-human vertebrates. For example, in humans, disease states associated with a disturbance of the synthesis or turnover of bone matrix may be diagnosed or monitored. In non-human vertebrates such as rodents, canines, bovines and felines, similar assessments may be made which may have use in veterinary science or in the assessment of pharmaceuticals.

The immunoassay requires the use of an antibody specific to type I collagen carboxyterminal telopeptide. A suitable antibody is one which has been raised against type I collagen carboxy-terminal cross-linked telopeptide, and is provided by the present invention. The telopeptide used in raising the antibody may be obtained from bone from a human or non-human vertebrate. In the more detailed discussion which follows, the collagen referred to is human collagen, but it will be appreciated that the facts may be applied appropriately to the collagen of any vertebrate.

DETAILED DESCRIPTION OF THE PREFERRED EMBODIMENTS

The cross-linked telopeptide used as the antigen for raising the antibody may be isolated from bone collagen. As indicated above the cross-linked fragment of the telopeptide is resistant to further degradation and is therefore a suitable choice as an antigen for raising the antibody.

The present invention also provides a process for isolating type I collagen carboxyterminal cross-linked telopeptide which comprises subjecting decalcified, insoluble bone tissue to denaturation, and chromatography using a plurality of steps of reverse phase separation with high performance liquid chromatography (HPLC), at least two of the separation steps being at different pH.

When type I collagen molecules are assembled into collagen fibers, intermolecular cross-links are formed between the carboxyterminal telopeptide region of one molecule and a particular site within the aminoterminal half of the triple-helical region of another molecule. These young cross-links mature slowly into multivalent cross-links, which in bone collagen have the chemical structure of pyridinoline or dehydropyridinoline and which are derived from two hydroxylysines or lysine or their aldehydes in the carboxyterminal telopeptides and one hydroxylysine reside (amino acid number 87 counted from the aminoterminus) in the helical region. Such pyridinoline structures have a characteristic fluorescence, on the basis of which peptides containing pyridinoline can be easily identified. These multivalent cross-links render the collagen insoluble in ordinary extraction procedures with either neutral or acidic solutions. Peptides still linked together by such cross-links can be isolated after subjecting decalcified insoluble bone tissue containing mainly cross-linked type I collagen after denaturation to a thorough digestion with a proteolytic enzyme such as trypsin or bacterial collagenase. The liberated cross-linked peptides are then purified by chromatographic methods preferably using a plurality of steps of reverse phase separation with high performance liquid chromatography (HPLC).

The isolated cross-linked telopeptide region coupled to a non-related protein, e.g. albumin, or intact type I collagen molecules, isolated in soluble form from salt or acidic extracts of tissues, may then be used to produce a specific antibody, e.g. by immunization of a suitable animal using techniques well known in the art, see, for example, "Immunochemistry of the Extracellular Matrix", ed. H Furthmayr, CRC Press, Boca Raton, U.S.A. 1982 and especially the articles by Furthmayr pp. 143-178, Linsenmayer et al. pp. 179-198 and Timpl et al. pp. 199-235. A highly specific type I collagen telopeptide antibody is best produced by the subcutaneous injection of type I collagen into test animals, e.g. rabbits in the case of polyclonal antibodies and mice for monoclonal antibodies, in the presence of a suitable adjuvant. The antibody may be monoclonal or polyclonal and of IgG or IgM-type.

The antibody produced by the above method is specific for the carboxyterminal telopeptide region, either cross-linked or not. The telopeptide measured in assaying a serum sample is cross-linked, since uncross-linked telopeptide is not resistant against further degradation during turnover of type I collagen and thus cannot be found in serum. However, the nature of the cross-link is not critical, since a peptide isolated from soft tissue type I collagen containing another type of cross-link (derived from lysine/hydroxylysine and also from histidine) can be detected by an antibody raised by the process described above. Also the same antibody can be used to measure soluble type I collagen molecules (e.g. during cell culture experiments etc.) which contain the telopeptide region, but are not cross-linked. Such situations are not encountered with serum samples, but may appear when other physiological or tissue fluids (ascitic fluid, wound fluid etc.) are assayed.

The immunoassay itself may be carried out using any method, but preferably a heterogenous method involving a phase separation step, such as one known by the initials RIA, ELISA, FIA, TR-FIA, EIA, and IRMA is used.

Preferably the assay is operated as a radioimmunoassay using isolated human cross-linked carboxyterminal type I collagen telopeptide, and an antibody specific to it. The telopeptide is labelled with a radionuclide, preferably iodine 125, using for example for the chloramine-T method, the free iodine being separated by a disposable reverse phase cartridge. Other methods of labelling using enzymatic, chromogenic, or fluorescent labels, e,g. europium, can also be used with the label being incorporated in a competitive standard, in the antibody, or in a separate reagent which complexes with the antibody or telopeptide. Known techniques which may be used in the immunoassay have been described in the literature, e.g. in the book "Immunochemistry of the Extracellular Matrix" mentioned above.

For example, in one method, i.e. a competitive binding assay, labelled cross-linked type I collagen carboxyterminal propeptide and the sample are both contacted with the antibody. The antigen-antibody complex so formed is separated from uncomplexed starting material and the complexed or uncomplexed label is assayed. The presence and/or amount of label is compared with a predetermined value wherein only labelled cross-linked type I collagen is used (i.e. wherein no competitive binding with product contained in a sample takes place). The antibody may also be bound to a solid support, whether before, during or after contacting with the sample. The resulting complex between the antibody and the type I collagen carboxyterminal telopeptide (whether contained in the sample, or previously isolated and pre-labelled as described immediately above) may then be separated from the medium in which the contacting takes place simply by separating the solid support from the medium.

Separation of the antigen-antibody complex may be accomplished by contacting the antigen-antibody complex with a further reagent, e.g., a second antibody specific to the first antibody and separating the antigen-antibody-antibody complex from the uncomplexed starting materials. Here again a solid support may-be employed, with the second antibody being bound to the support. Other immobilization approaches such as biotin/(strept)avidin complexes can also be employed.

Separation of antibody-containing complexes from the contacting medium may also be accomplished by such known methods as filtration or centrifuging.

The immunoassay method of the invention permits the determination of type I collagen degradation products in human serum or other body fluids. The concentration of the cross-linked telopeptide in normal serum is about 1.5 to 4.2 micrograms/liter and is raised e.g. in prostatic or breast carcinoma patients with osteolytic metastases, who may have as much as a twentyfold increase in the concentration of the type I collagen degradation products. The assay method is capable of detecting 0.5 microgram/liter of the cross-linked telopeptide.

The following Examples illustrate the invention.

EXAMPLE I

Preparation of cross-linked carboxyterminal telopeptide of type I collagen from human bone or from bone of experimental animal and production of a specific antibody against it:

First, insoluble type I collagen is isolated from human or experimental animal (.e.g. rat, guinea pig, dog, bovine) bone. In the case of human bone, one cm slices of femoral bone are obtained from the head of a femur removed during elective hip joint replacement surgery. In the case of experimental animal, the femoral bone is prepared after decapitation of the animal. The bones are extracted with acetone to remove the fat present in bone marrow. After drying in air, the slices are cut into smaller pieces and finally pulverized under liquid nitrogen using a mineral mill (Raetsch AG, Germany). Non-collagenous proteins are extracted at +4° C. for 24 h by 4M guanidine/HCl in 50 mM Tris/HCl-buffer, pH 7.4, containing protease-inhibitors (0.1M aminocapronic acid, 5 mM benzamidine/HCl and 1 mM phenylmethylsulphonylfluoride). After extraction the bone powder is washed several times with distilled water to remove the traces of the extraction buffer. Then the still mineralized bone powder is demineralized by extraction at +4° C. for 24 h with 0.5M EDTA adjusted to pH 7.4 and containing 6M urea. The extraction is repeated twice. The insoluble residue is collected by centrifugation (15000× g for 30 min.) and washed several times with distilled water to remove the traces of the extraction buffer. Thereafter the residue is lyophilized. About one g of insoluble collagen can be obtained from a one cm slice of human femoral bone.

For the preparation of degradation peptides 2 g of insoluble bone collagen is suspended in 100 ml of 0.2M ammonium bicarbonate and denatured at +70° C. for 30 min. After decreasing the temperature of the solution to +37°C. the material is digested at +37° C. for 8 h with bacterial collagenase (CLSPA grade, Worthington, USA) using 10 mg of the enzyme. After renewed denaturation (30 min. at +70° C.) more enzyme (10 mg) is added and the mixture is incubated at +37° C. for another 12 h. After digestion, the mixture is centrifuged (15000× g for 30 min) to remove undigested insoluble material. Then the supernatant is adjusted to pH 2.5 with concentrated HCl, and isopropanol is added to the final concentration of 20%. This mixture (about 100 ml) is then passed in 5 ml portions through a preparative Sep-Pak® $C_{18}$ cartridge. The cross-linked carboxyterminal telopeptide of type I collagen is bound to the cartridge from which it is detached with 3 ml of 50% isopropanol in 0.1M acetic acid. The eluate is then lyophilized to dryness. A mixture containing about 40 mg of peptides is obtained from 2 g of insoluble collagen.

The purification of the cross-linked carboxyterminal telopeptide of type I collagen is performed using two different reverse phase steps in high performance liquid chromatography (HPLC). The lyophilized peptide mixture is first dissolved in 0.1% trifluoracetic acid and applied to a $C_{18}$ reverse phase column (Vydac® 218TP1010). The bound peptides are eluted with increasing concentrations of isopropanol (10–70%, 0–45 min). The eluate is monitored for the fluorescence characteristic for pyridinoline cross-links (excitation 295 nm, emission 395 nm). The fluorescent peptide peak containing the cross-linked carboxyterminal telopeptide of type I collagen is collected and lyophilized. Then the peptide (which still contains a minor amount of other contaminating peptides) is dissolved in 50 mM ammonium acetate, pH 7.4, and applied to a $C_{18}$ pH stable reverse phase column (Vydac® 228TP104). The bound peptide is eluted with increasing concentrations of acetonitrile (0–90%, 0–45 min.). The eluate is monitored for fluorescence as above and the now homogenous cross-linked carboxyterminal telopeptide of type I collagen is collected and lyophilized. The origin and identity of the peptide are verified by N-terminal amino acid sequencing. The following sequences can be obtained for the cross-linked human peptide derived from two carboxyterminal telopeptides of α1-chains of type I collagen (Seq. ID[1]) and a region from the helical part of either α1-chain or α2-chain of type I collagen (Seq. ID[2] or [3]) as shown in Table 1, where Hyp is hydroxyproline, Hyl is hydroxylysine and indicates the position of the cross-link.

complete adjuvant. A two ml aliquot of the suspension is given intradermally in the back of a rabbit in 50 different places. A similar booster injection is given after three weeks and, after testing the antiserum for binding of radioactively labelled antigen, repeated if necessary. When mice are immunized only 0.1 ml of a similar suspension is given in the back of a mouse. A similar booster injection is given after three weeks and another is given intraperitoneally a few days before removing the spleen for hybridoma production.

EXAMPLE II

Performance of the equilibrium type of radioimmunoassay:

Five micrograms of the cross-linked carboxyterminal telopeptide of type I collagen produced as described in Example I are labelled with 1 millicurie of iodine-125 using chloramine-T (5 micrograms). The free iodine is removed, after acidifying the solution with 0.1M acetic acid, with a preparative Sep-Pak® $C_{18}$ cartridge. The labelled peptide is eluted from the cartridge with 50% isopropanol of 0.1M acetic acid.

Antibody binding curves are prepared with 50000 radioactivity counts per minute of the labelled cross-linked radioactivity counts per minute of the labelled cross-linked telopeptide. The telopeptide concentration in an unknown sample of serum or other body fluid is determined in the following radioimmuno inhibition assay. A pretested amount of the antiserum is incubated with the unknown sample and 50000 counts per minute of the tracer for 2 hours at 37° C. Then a second antibody against rabbit gamma globulin in 1.2M $(NH_4)_2SO_4$ is added and after 30 min. incubation at +4° C., an antigen bound in the immune complex is separated by centrifugation from the solution. The inhibition activity of the unknown sample is compared with the activity of the standard concentrations of unlabelled cross-linked carboxyterminal telopeptide of type I collagen.

TABLE 1

| | |
|---|---|
| Gly Pro Hyp Ser Ala Gly Phe Asp Phe Ser Phe Leu Pro Gln Pro Pro Glu Glu Lys Ala His Asp Gly Gly Arg Tyr Tyr Arg Ala<br>    5           10            15              20           25 | Seq.ID[1] |
| α1-chain of type I collagen | |
| Gly Pro Hyp Ser Ala Gly Phe Asp Phe Ser Phe Leu Pro Gln Pro Pro Glu Glu Lys Ala His Asp Gly Gly Arg Tyr Tyr Arg Ala<br>    5           10            15              20           25 | Seq.ID[1] |
| AND EITHER α1-chain of type I collagen | |
| Gly Leu Hyp Gly Thr Ala Gly Leu Hyp Gly Met Hyl Gly His Arg<br>            5              10                15 | Seq.ID[2] |
| OR α2-chain of type I collagen | |
| Gly Phe Hyp Gly Thr Hyp Gly Leu Hyp Gly Phe Hyl Gly Ile Arg<br>            5              10                15 | Seq.ID[3] |

Depending on the enzyme used to liberate the peptide and varying also between different preparations the starting sequences may be a few amino acids longer or shorter. However, this does not affect the assay, since the immunological determinants measured are around the cross-link (marked ) in the α1-chain telopeptide region.

The antiserum specific for the carboxyterminal telopeptide can be obtained by immunizing rabbits with 0.1 mg of the purified cross-linked telopeptide solubilized in 1 ml 0.2M $NH_4HCO_3$ and mixed together with 1 ml of Freund's

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE:

( v ) FRAGMENT TYPE: C-terminal ( v i ) ORIGINAL SOURCE:
        ( A ) ORGANISM: human
        ( F ) TISSUE TYPE: bone ( i x ) FEATURE:
        ( D ) OTHER INFORMATION: Sequence is part of
            cross-linked telopeptide
            derived from Type I collagen.
            Xaa at position 3 is 4Hyp.

( x i ) SEQUENCE DESCRIPTION: SEQ ID NO:1:

```
Gly Pro Xaa Ser Ala Gly Phe Asp Phe Ser Phe Leu Pro Gln Pro Pro
1               5                   10                  15
Glu Glu Lys Ala His Asp Gly Gly Arg Tyr Tyr Arg Ala
            20                  25
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE:

( v ) FRAGMENT TYPE: C-terminal ( v i ) ORIGINAL SOURCE:
        ( A ) ORGANISM: human
        ( F ) TISSUE TYPE: bone ( i x ) FEATURE:
        ( D ) OTHER INFORMATION: Sequence is part of
            cross-linked telopeptide
            derived from Type I collagen.
            Xaa at position 3 and 9 is
            4Hyp. Xaa at position 12 is
            Hyl.

( x i ) SEQUENCE DESCRIPTION: SEQ ID NO:2:

```
Gly Leu Xaa Gly Thr Ala Gly Leu Xaa Gly Met Xaa Gly His Arg
1               5                   10                  15
```

( 2 ) INFORMATION FOR SEQ ID NO:3:

( i ) SEQUENCE CHARACTERISTICS:

```
            ( A ) LENGTH: 15 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE:

( v ) FRAGMENT TYPE: C-terminal ( v i ) ORIGINAL SOURCE:
                ( A ) ORGANISM: human
                ( F ) TISSUE TYPE: bone ( i x ) FEATURE:
                ( D ) OTHER INFORMATION: Sequence is part of
                      cross-linked telopeptide
                      derived from Type I collagen.
                      Xaa at positions 3, 6 and 9 is
                      4Hyp. Xaa at position 12 is
                      Hyl.

( x i ) SEQUENCE DESCRIPTION: SEQ ID NO:3:

Gly  Phe  Xaa  Gly  Thr  Xaa  Gly  Leu  Xaa  Gly  Phe  Xaa  Gly  Ile  Arg
   1              5                        10                       15
```

We claim:

1. A method for testing for the presence or level of a type I collagen degradation product in a sample other than urine, comprising combining with the sample an antibody which specifically binds to a peptide derived from type I collagen carboxyterminal telopeptide selected from the group consisting of Gly Pro Hyp Ser Ala Gly Phe Asp Phe Ser Phe Leu Pro Gln Pro
        5          10          15

Gly Pro Hyp Ser Ala Gly Phe Asp Phe Ser Phe Leu Pro Gln Pro
        5          10          15

Gly Leu Hyp Gly Thr Ala Gly Leu
                      5

Pro Glu Glu Lys Ala His Asp Gly Gly Arg Tyr Tyr Arg Ala
              |  20              25

Pro Glu Glu Lys Ala His Asp Gly Gly Arg Tyr Tyr Arg Ala
              |  20              25

Hyp Gly Met Hyl Gly His Arg
          10          15 or

Gly Pro Hyp Ser Ala Gly Phe Asp Phe Ser Phe Leu Pro Gln Pro
        5          10          15

Gly Pro Hyp Ser Ala Gly Phe Asp Phe Ser Phe Leu Pro Gln Pro
        5          10          15

Gly Phe Hyp Gly Thr Hyp Gly Leu
                      5

Pro Glu Glu Lys Ala His Asp Gly Gly Arg Tyr Tyr Arg Ala
              |  20              25

Pro Glu Glu Lys Ala His Asp Gly Gly Arg Tyr Tyr Arg Ala,
              |  20              25

Hyp Gly Phe Hyl Gly Ile Arg
          10          15 wherein the antibody binds an immunological determinant comprising amino acids other than the cross-links in the peptide, and detecting the binding of the antibody to the type I collagen degradation product.

2. A method for assaying a type I collagen degradation product, which comprises contacting in any order (i) a sample other than urine which is known or suspected to contain such product; (ii) an antibody which specifically binds to a peptide derived from type I collagen carboxyterminal telopeptide selected from the group consisting of Gly Pro Hyp Ser Ala Gly Phe Asp Phe Ser Phe Leu Pro Gln Pro
        5          10          15

Gly Pro Hyp Ser Ala Gly Phe Asp Phe Ser Phe Leu Pro Gln Pro
        5          10          15

Gly Leu Hyp Gly Thr Ala Gly Leu
                      5

Pro Glu Glu Lys Ala His Asp Gly Gly Arg Tyr Tyr Arg Ala
              |  20              25

Pro Glu Glu Lys Ala His Asp Gly Gly Arg Tyr Tyr Arg Ala
              |  20              25

Hyp Gly Met Hyl Gly His Arg
          10          15 or

Gly Pro Hyp Ser Ala Gly Phe Asp Phe Ser Phe Leu Pro Gln Pro
        5          10          15

Gly Pro Hyp Ser Ala Gly Phe Asp Phe Ser Phe Leu Pro Gln Pro
        5          10          15

Gly Phe Hyp Gly Thr Hyp Gly Leu
                      5

Pro Glu Glu Lys Ala His Asp Gly Gly Arg Tyr Tyr Arg Ala
              |  20              25

Pro Glu Glu Lys Ala His Asp Gly Gly Arg Tyr Tyr Arg Ala,
              |  20              25

Hyp Gly Phe Hyl Gly Ile Arg
          10          15 wherein the antibody binds to an immunological determinant comprising amino acids other than the cross-links in the peptide, and (iii) a label; under conditions such that the label becomes bound in an antibody-containing complex in an amount which depends on the amount of type I collagen degradation product in said sample, and then assaying the bound and/or unbound label to determine the presence or level of the type I collagen degradation product in said sample.

3. A method according to claim 2, wherein labelled type I collagen carboxyterminal telopeptide and the sample are both contacted with said antibody, the antigen-antibody complexes so formed are separated from uncomplexed starting materials, and the complexed or the uncomplexed label is assayed.

4. A method according to claim 3 wherein the antigen-antibody complex is contacted with a second antibody which specifically binds to the first antibody, and the antigen-antibody-antibody complex so formed is separated from the uncomplexed starting materials.

5. A method according to any one of claims 2 to 4 wherein the label is a radioactive, enzymatic, or fluorescent label.

6. A method according to any one of claims 2 or 3 wherein the antibody is immobilized to a solid support, and the antigen-antibody complex formed is separated from a medium in which the contact takes place by separating said solid support from said medium.

7. A method according to claim 4 wherein the second antibody is immobilized to a solid support, and the antigen-antibody-antibody complex so formed is separated from a medium in which the contact takes place by separating said solid support from said medium.

8. A method according to any one of claims 2–4 wherein the antibody when specifically binds to a peptide derived from type I collagen carboxyterminal telopeptide is raised against type I collagen carboxyterminal cross-linked telopeptide.

9. A method according to claim 8 in which the telopeptide used to raise the antibody was obtained from bone from a human or animal vertebrate.

10. A method according to any one of claims 1 to 4 in which the antibody when specifically binds to a peptide derived from type I collagen carboxyterminal telopeptide is a monoclonal antibody.

11. A kit suitable for use in carrying out an assay method according to claim 2 comprising an antibody which specifically binds to a peptide derived from type I collagen carboxyterminal telopeptide selected from group consisting of

```
Gly Pro Hyp Ser Ala Gly Phe Asp Phe Ser Phe Leu Pro Gln Pro
 5                10                15
Gly Pro Hyp Ser Ala Gly Phe Asp Phe Ser Phe Leu Pro Gln Pro
 5                10                15
        Gly Leu Hyp Gly Thr Ala Gly Leu
                    5
        Pro Glu Glu Lys Ala His Asp Gly Gly Arg Tyr Tyr Arg Ala
                    |   20                25
        Pro Glu Glu Lys Ala His Asp Gly Gly Arg Tyr Tyr Arg Ala
                    |   20                25
        Hyp Gly Met Hyl Gly His Arg
                10              15
``` or

```
Gly Pro Hyp Ser Ala Gly Phe Asp Phe Ser Phe Leu Pro Gln Pro
 5                10                15
Gly Pro Hyp Ser Ala Gly Phe Asp Phe Ser Phe Leu Pro Gln Pro
 5                10                15
        Gly Phe Hyp Gly Thr Hyp Gly Leu
                    5
        Pro Glu Glu Lys Ala His Asp Gly Gly Arg Tyr Tyr Arg Ala
                    |   20                25
        Pro Glu Glu Lys Ala His Asp Gly Gly Arg Tyr Tyr Arg Ala,
                    |   20                25
        Hyp Gly Phe Hyl Gly Ile Arg
                10              15
``` wherein the antibody binds to an immunological determinant comprising amino acids other than the cross-links in the peptide, and a label.

12. A kit suitable for use in carrying out an assay method according to claim 3 comprising an antibody which specifically binds to a peptide derived from type I collagen carboxyterminal telopeptide selected from the group consisting of

```
Gly Pro Hyp Ser Ala Gly Phe Asp Phe Ser Phe Leu Pro Gln Pro Pro Glu Glu Lys Ala His Asp Gly Gly Arg Tyr Tyr Arg Ala
 5                10                15              |  20                25
Gly Pro Hyp Ser Ala Gly Phe Asp Phe Ser Phe Leu Pro Gln Pro Pro Glu Glu Lys Ala His Asp Gly Gly Arg Tyr Tyr Arg Ala
 5                10                15              |  20                25
        Gly Leu Hyp Gly Thr Ala Gly Leu Hyp Gly Met Hyl Gly His Arg
                    5                       10              15
``` and

```
Gly Pro Hyp Ser Ala Gly Phe Asp Phe Ser Phe Leu Pro Gln Pro Pro Glu Glu Lys Ala His Asp Gly Gly Arg Tyr Tyr Arg Ala
 5                10                15              |  20                25
Gly Pro Hyp Ser Ala Gly Phe Asp Phe Ser Phe Leu Pro Gln Pro Pro Glu Glu Lys Ala His Asp Gly Gly Arg Tyr Tyr Arg Ala
 5                10                15              |  20                25
        Gly Phe Hyp Gly Thr Hyp Gly Leu Hyp Gly Phe Hyl Gly Ile Arg
                    5                       10              15
``` wherein the antibody binds to an immunological determinant comprising amino acids other than the cross-links in the peptide, and labelled type I collagen carboxyterminal telopeptide.

13. A kit suitable for use in carrying out an assay method according to claim 4 comprising a first antibody which specifically binds to a peptide derived from type I collagen carboxyterminal telopeptide selected from the group consisting of Gly Pro Hyp Ser Ala Gly Phe Asp Phe Ser Phe Leu Pro Gln Pro Pro Glu Glu Lys Ala His Asp Gly Gly Arg Tyr Tyr Arg Ala
              5             10            15            20            25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala
              5             10            15            20            25

Gly Leu Hyp Gly Thr Ala Gly Leu Hyp Gly Met Hyl Gly His Arg
                     5                 10             15 and

Gly Pro Hyp Ser Ala Gly Phe Asp Phe Ser Phe Leu Pro Gln Pro Pro Glu Glu Lys Ala His Asp Gly Gly Arg Tyr Tyr Arg Ala
              5             10            15            20            25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala
              5             10            15            20            25

Gly Phe Hyp Gly Thr Hyp Gly Leu Hyp Gly Phe Hyl Gly Ile Arg
                     5                 10             15 wherein the antibody binds to an immunological determinant comprising amino acids other than the cross-links in the peptide, labelled type I collagen carboxyterminal telopeptide, and a second antibody which specifically binds to the first antibody.

14. A kit suitable for use in carrying out an assay method according to claim 6 comprising an antibody which specifically binds to a peptide derived from type I collagen carboxyterminal telopeptide selected from the group consisting of Gly Pro Hyp Ser Ala Gly Phe Asp Phe Ser Phe Leu Pro Gln Pro
              5             10            15

Gly Pro Hyp Ser Ala Gly Phe Asp Phe Ser Phe Leu Pro Gln Pro
              5             10            15

Gly Leu Hyp Gly Thr Ala Gly Leu
                     5

Pro Glu Glu Lys Ala His Asp Gly Gly Arg Tyr Tyr Arg Ala
              20            25

Pro Glu Glu Lys Ala His Asp Gly Gly Arg Tyr Tyr Arg Ala
              20            25

Hyp Gly Met Hyl Gly His Arg
 10            15 or

Gly Pro Hyp Ser Ala Gly Phe Asp Phe Ser Phe Leu Pro Gln Pro
              5             10            15

Gly Pro Hyp Ser Ala Gly Phe Asp Phe Ser Phe Leu Pro Gln Pro
              5             10            15

Gly Phe Hyp Gly Thr Hyp Gly Leu
                     5

-continued

Pro Glu Glu Lys Ala His Asp Gly Gly Arg Tyr Tyr Arg Ala
              20            25

Pro Glu Glu Lys Ala His Asp Gly Gly Arg Tyr Tyr Arg Ala,
              20            25

Hyp Gly Phe Hyl Gly Ile Arg
 10            15 wherein the antibody binds to an immunological determinant comprising amino acids other than the cross-links in the peptide, a label, and a solid support to which is immobilized the antibody.

15. A kit suitable for use in carrying out an assay method according to claim 7 comprising a first antibody which specifically binds to a peptide derived from type I collagen carboxyterminal telopeptide selected from the group consisting of Gly Pro Hyp Ser Ala Gly Phe Asp Phe Ser Phe Leu Pro Gln Pro
              5             10            15

Gly Pro Hyp Ser Ala Gly Phe Asp Phe Ser Phe Leu Pro Gln Pro
              5             10            15

Gly Leu Hyp Gly Thr Ala Gly Leu
                     5

Pro Glu Glu Lys Ala His Asp Gly Gly Arg Tyr Tyr Arg Ala
              20            25

Pro Glu Glu Lys Ala His Asp Gly Gly Arg Tyr Tyr Arg Ala
              20            25

Hyp Gly Met Hyl Gly His Arg
 10            15 or

Gly Pro Hyp Ser Ala Gly Phe Asp Phe Ser Phe Leu Pro Gln Pro
              5             10            15

Gly Pro Hyp Ser Ala Gly Phe Asp Phe Ser Phe Leu Pro Gln Pro
              5             10            15

Gly Phe Hyp Gly Thr Hyp Gly Leu
                     5

Pro Glu Glu Lys Ala His Asp Gly Gly Arg Tyr Tyr Arg Ala
              20            25

Pro Glu Glu Lys Ala His Asp Gly Gly Arg Tyr Tyr Arg Ala,
              20            25

Hyp Gly Phe Hyl Gly Ile Arg
 10            15 wherein the antibody binds to an immunological determinant comprising amino acids other than the cross-links in the peptide, a second antibody which specifically binds to the first antibody, a label, and a solid support to which is immobilized the first or second antibody.

16. An antibody raised against type I collagen carboxy-terminal cross-linked telopeptide which specifically binds to a peptide selected from the group consisting of Gly Pro Hyp Ser Ala Gly Phe Asp Phe Ser Phe Leu Pro Gln Pro
 5                  10              15

Gly Pro Hyp Ser Ala Gly Phe Asp Phe Ser Phe Leu Pro Gln Pro
 5                  10              15

Gly Leu Hyp Gly Thr Ala Gly Leu
                        5

Pro Glu Glu Lys Ala His Asp Gly Gly Arg Tyr Tyr Arg Ala
          |  20                25
          |

Pro Glu Glu Lys Ala His Asp Gly Gly Arg Tyr Tyr Arg Ala
          |  20                25
          |

Hyp Gly Met Hyl Gly His Arg
 10              15 or

Gly Pro Hyp Ser Ala Gly Phe Asp Phe Ser Phe Leu Pro Gln Pro Pro Glu Glu Lys Ala His Asp Gly Gly Arg Tyr Tyr Arg Ala
 5                  10              15                          |  20                25
                                                                |

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
 5                  10              15                          |  20                25
                                                                |

Gly Phe Hyp Gly Thr Hyp Gly Leu Hyp Gly Phe Hyl Gly Ile Arg
                        5              10              15

-continued

Gly Pro Hyp Ser Ala Gly Phe Asp Phe Ser Phe Leu Pro Gln Pro
 5                  10              15

Gly Pro Hyp Ser Ala Gly Phe Asp Phe Ser Phe Leu Pro Gln Pro
 5                  10              15

Gly Phe Hyp Gly Thr Hyp Gly Leu
                        5

Gly Pro Hyp Ser Ala Gly Phe Asp Phe Ser Phe Leu Pro Gln Pro Pro Glu Glu Lys Ala His Asp Gly Gly Arg Tyr Tyr Arg Ala
 5                  10              15                          |  20                25
                                                                |

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
 5                  10              15                          |  20                25
                                                                |

Gly Phe Hyp Gly Thr Hyp Gly Leu Hyp Gly Phe Hyl Gly Ile Arg
                        5              10              15

-continued

Pro Glu Glu Lys Ala His Asp Gly Gly Arg Tyr Tyr Arg Ala
          |  20                25
          |

Pro Glu Glu Lys Ala His Asp Gly Gly Arg Tyr Tyr Arg Ala,
          |  20                25
          |

Hyp Gly Phe Hyl Gly Ile Arg
 10              15 wherein the antibody binds to an immunological determinant comprising amino acids other than the cross-links in the peptide.

17. An antibody according to claim 16 in which the telopeptide is obtained from bone from a human or non-human vertebrate.

18. An antibody according to any one of claim 16 or 17 wherein the antibody is a monoclonal antibody.

19. A method for testing for the presence or level of a type I collagen degradation product in a sample other than urine, comprising combining with the sample an antibody which specifically bind to wherein the antibody binds to an immunological determinant comprising amino acids other than the cross-links in the peptide, and detecting the binding of the antibody to the type I collagen degradation product.

20. A method for assaying a type I collagen degradation product, which comprises contacting in any order (i) a sample other than urine which is known or suspected to contain such product; (ii) an antibody which specifically binds to wherein the antibody binds to an immunological determinant comprising amino acids other than the cross-links in the peptide, and (iii) a label, under conditions such that the label becomes bound in an antibody-containing complex in an amount which depends on the amount of collagen degradation product in said sample, and then assaying the bound and/or unbound label to determine the presence or level of the type I collagen degradation product in said sample.

21. A kit suitable for use in carrying out an assay method according to claim 20 comprising an antibody which specifically binds to Gly Pro Hyp Ser Ala Gly Phe Asp Phe Ser Phe Leu Pro Gln Pro Pro Glu Glu Lys Ala His Asp Gly Gly Arg Tyr Tyr Arg Ala
     5              10             15            |  20            25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
     5              10             15            |  20            25
                                                 |
           Gly Phe Hyp Gly Thr Hyp Gly Leu Hyp Gly Phe Hyl Gly Ile Arg
                     5                  10                 15 wherein the antibody binds to an immunological determinant comprising amino acids other than the cross-links in the peptide, and a label.

22. An antibody raised against type I collagen carboxy-terminal cross-linked telopeptide which specifically binds to Gly Pro Hyp Ser Ala Gly Phe Asp Phe Ser Phe Leu Pro Gln Pro Pro Glu Glu Lys Ala His Asp Gly Gly Arg Tyr Tyr Arg Ala
     5              10             15            |  20            25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
     5              10             15            |  20            25
                                                 |
           Gly Phe Hyp Gly Thr Hyp Gly Leu Hyp Gly Phe Hyl Gly Ile Arg
                     5                  10                 15 wherein the antibody binds to an immunological determinant comprising amino acids other than the cross-links in the peptide.

23. A method for testing for the presence or level of a type I collagen degradation product in a sample other than urine, comprising combining with the sample an antibody which specifically binds to Gly Pro Hyp Ser Ala Gly Phe Asp Phe Ser Phe Leu Pro Gln Pro Pro Glu Glu Lys Ala His Asp Gly Gly Arg Tyr Tyr Arg Ala
     5              10             15            |  20            25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
     5              10             15            |  20            25
                                                 |
           Gly Leu Hyp Gly Thr Ala Gly Leu Hyp Gly Met Hyl Gly His Arg
                     5                  10                 15 wherein the antibody binds to an immunological determinant comprising amino acids other than the cross-links in the peptide, and detecting the binding of the antibody to the type I collagen degradation product.

24. A method for assaying a type I collagen degradation product, which comprises contacting in any order (i) a sample other than urine which is known or suspected to contain such product; (ii) an antibody which specifically binds to Gly Pro Hyp Ser Ala Gly Phe Asp Phe Ser Phe Leu Pro Gln Pro Pro Glu Glu Lys Ala His Asp Gly Gly Arg Tyr Tyr Arg Ala
     5              10             15            |  20            25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
     5              10             15            |  20            25
                                                 |
           Gly Leu Hyp Gly Thr Ala Gly Leu Hyp Gly Met Hyl Gly His Arg
                     5                  10                 15 wherein the antibody binds to an immunological determinant comprising amino acids other than the cross-links in the peptide, and (iii) a label, under conditions such that the label becomes bound in an antibody-containing complex in an amount which depends on the amount of collagen degradation product in said sample, and then assaying the bound and/or unbound label to determine the presence or level of the type I collagen degradation product in said sample.

25. A kit suitable for use in carrying out an assay method according to claim 24 comprising an antibody which specifically binds to Gly Pro Hyp Ser Ala Gly Phe Asp Phe Ser Phe Leu Pro Gln Pro Pro Glu Glu Lys Ala His Asp Gly Gly Arg Tyr Tyr Arg Ala
         5                 10              15              20              25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
         5                 10              15              20              25

Gly Leu Hyp Gly Thr Ala Gly Leu Hyp Gly Met Hyl Gly His Arg
                             5              10              15 wherein the antibody binds to an immunological determinant comprising amino acids other than the cross-links in the peptide, and a label.

26. An antibody raised against type I collagen carboxy-terminal cross-linked telopeptide which specifically binds to Gly Pro Hyp Ser Ala Gly Phe Asp Phe Ser Phe Leu Pro Gln Pro Pro Glu Glu Lys Ala His Asp Gly Gly Arg Tyr Tyr Arg Ala
         5                 10              15              20              25

Gly Pro Hyp Ser Ala Gly Phe Asp Phe Ser Phe Leu Pro Gln Pro Pro Glu Glu Lys Ala His Asp Gly Gly Arg Tyr Tyr Arg Ala,
         5                 10              15              20              25

Gly Leu Hyp Gly Thr Ala Gly Leu Hyp Gly Met Hyl Gly His Arg
                             5              10              15 wherein the antibody binds to an immunological determinant comprising amino acids other than the cross-links in the peptide.

27. A method according to claims 1, 2, 19, 20, 23 or 24 wherein the peptide is obtained by subjecting denatured bone collagen to digestion with a proteolytic enzyme selected from the group consisting of bacterial collagenase and trypsin.

28. A kit according to claims 12, 13, 15, 21 or 25 wherein the peptide is obtained by subjecting denatured bone collagen to digestion with a proteolytic enzyme selected from the group consisting of bacterial collagenase and trypsin.

29. An antibody according to claim 16 or claim 26 wherein the peptide is obtained by subjecting denatured bone collagen to digestion with a proteolytic enzyme selected from the group consisting of bacterial collagenase and trypsin.

* * * * *

UNITED STATES PATENT AND TRADEMARK OFFICE
CERTIFICATE OF CORRECTION

PATENT NO. : 5,538,853
DATED : July 23, 1996
INVENTOR(S) : Risteli et al.

It is certified that error appears in the above-identified patent and that said Letters Patent is hereby corrected as shown below:

In the Claims:

Column 9,
Line 65: "binds an" should read -- binds to an --

Column 11,
Line 32: "when" should read -- which --
Line 40: "when" should read -- which --

Column 16,
Line 12: "bind" should read -- binds --
Sequence running cross-column at mid-page should be right-aligned below text for claim 19 (col. 16)
Sequence running cross-column near bottom of page should be right-aligned below text for claim 20 (col. 16)

IN THE SPECIFICATION:

Column 1,
Line 6: "1992 now" should read -- 1992, now --

Column 3,
Line 42: "e.g." should read -- e.g. --

Signed and Sealed this

Seventh Day of August, 2001

Attest:

NICHOLAS P. GODICI
*Attesting Officer*  *Acting Director of the United States Patent and Trademark Office*

UNITED STATES PATENT AND TRADEMARK OFFICE
CERTIFICATE OF CORRECTION

PATENT NO. : 5,538,853
DATED : July 23, 1996
INVENTOR(S) : Risteli et al.

It is certified that error appears in the above-identified patent and that said Letters Patent is hereby corrected as shown below:

Column 20,
Line 10, "claims 12, 13, 15, 21, or 25" should read -- claims 11, 12, 13, 14, 15, 21 or 25 --.

Signed and Sealed this

First Day of January, 2002

Attest:

Attesting Officer

JAMES E. ROGAN
Director of the United States Patent and Trademark Office